United States Patent
Vardi et al.

(10) Patent No.: US 8,211,167 B2
(45) Date of Patent: Jul. 3, 2012

(54) METHOD OF USING A CATHETER WITH ATTACHED FLEXIBLE SIDE SHEATH

(75) Inventors: Gil M. Vardi, Chesterfield, MO (US); Charles J. Davidson, Winnetka, IL (US); Eric Williams, Fairfield, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1557 days.

(21) Appl. No.: 10/762,562

(22) Filed: Jan. 23, 2004

(65) Prior Publication Data

US 2005/0245941 A1 Nov. 3, 2005

Related U.S. Application Data

(62) Division of application No. 09/455,299, filed on Dec. 6, 1999, now Pat. No. 6,692,483.

(51) Int. Cl.
*A61F 2/84* (2006.01)
(52) U.S. Cl. .................. 623/1.35; 623/903; 604/529
(58) Field of Classification Search ............... 623/1.11, 623/1.12, 903, 1.35
See application file for complete search history.

(56) References Cited

U.S. PATENT DOCUMENTS

| | | |
|---|---|---|
| 1,596,754 A | 8/1926 | Moschelle |
| 3,657,744 A | 4/1972 | Ersek |
| 3,872,893 A | 3/1975 | Roberts |
| 4,140,126 A | 2/1979 | Choudhury |
| 4,309,994 A | 1/1982 | Grunwald |
| 4,410,476 A | 10/1983 | Redding et al. |
| 4,413,989 A | 11/1983 | Schjeldahl |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |

(Continued)

FOREIGN PATENT DOCUMENTS

CA 2318314 7/1999

(Continued)

OTHER PUBLICATIONS

Serruys et al., *The New England Journal of Medicine*, vol. 331, No. 8, pp. 489-495 (1994).

(Continued)

*Primary Examiner* — Brian E. Pellegrino
(74) *Attorney, Agent, or Firm* — Seager, Tufte & Wickhem LLC

(57) ABSTRACT

A method of positioning a main stent at a vessel bifurcation includes positioning a main guidewire in the main vessel; and advancing a stent delivery system to a position proximate the bifurcation. The stent delivery system includes a catheter with a flexible side sheath attached thereto and a main stent positioned over the catheter. The flexible side sheath is positioned to pass through the side opening in the main stent. The method also includes advancing a branch guidewire through the flexible side sheath and into the branch vessel; and subsequently, advancing the catheter over the main guidewire while advancing the flexible side sheath over the branch guidewire while viewing relative movement of a marker positioned on the flexible side sheath with respect to at least one marker positioned on the catheter.

1 Claim, 13 Drawing Sheets

U.S. PATENT DOCUMENTS

| | | |
|---|---|---|
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,946,464 A | 8/1990 | Pevsner |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Ansel |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,437,638 A | 8/1995 | Bowman |
| 5,443,497 A | 8/1995 | Venbrux |
| 5,445,624 A | 8/1995 | Jiminez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,489,271 A | 2/1996 | Anderson |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau |
| 5,507,769 A | 4/1996 | Marin et al. |
| 5,514,154 A | 5/1996 | Lau et al. |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,569,295 A | 10/1996 | Lam |
| 5,571,087 A | 11/1996 | Ressemann et al. |
| 5,575,771 A | 11/1996 | Walinsky |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,679,400 A | 10/1997 | Tuch |
| 5,690,642 A | 11/1997 | Osborne et al. |
| 5,693,084 A | 12/1997 | Chutter |
| 5,693,086 A | 12/1997 | Goicoechea et al. |
| 5,697,971 A | 12/1997 | Fischell et al. |
| 5,707,354 A | 1/1998 | Salmon |
| 5,709,713 A | 1/1998 | Evans et al. |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |

| | | | | | | |
|---|---|---|---|---|---|---|
| 5,855,600 | A | 1/1999 | Alt | 6,273,913 B1 | 8/2001 | Wright et al. |
| 5,855,601 | A | 1/1999 | Bessler et al. | 6,287,314 B1 | 9/2001 | Lee et al. |
| 5,865,178 | A | 2/1999 | Yock | 6,290,673 B1 | 9/2001 | Shanley |
| 5,868,777 | A | 2/1999 | Lam | 6,293,967 B1 | 9/2001 | Shanley |
| 5,871,537 | A | 2/1999 | Holman et al. | 6,299,634 B1 | 10/2001 | Bergeron |
| 5,891,133 | A | 4/1999 | Murphy-Chutorian | 6,302,906 B1 | 10/2001 | Goicoechea et al. |
| 5,897,588 | A | 4/1999 | Hull et al. | 6,309,412 B1 | 10/2001 | Lau et al. |
| 5,906,640 | A | 5/1999 | Penn et al. | 6,309,414 B1 | 10/2001 | Rolando et al. |
| 5,907,893 | A | 6/1999 | Zadno-Azizi et al. | 6,312,459 B1 | 11/2001 | Huang et al. |
| 5,913,895 | A | 6/1999 | Burpee et al. | 6,325,821 B1 | 12/2001 | Gaschino et al. |
| 5,913,897 | A | 6/1999 | Corso, Jr. et al. | 6,325,826 B1 | 12/2001 | Vardi et al. |
| 5,921,958 | A | 7/1999 | Ressemann et al. | 6,334,870 B1 | 1/2002 | Her et al. |
| 5,922,020 | A | 7/1999 | Klein et al. | 6,346,089 B1 | 2/2002 | Dibie |
| 5,928,248 | A | 7/1999 | Acker | 6,361,544 B1 | 3/2002 | Wilson et al. |
| 5,938,682 | A | 8/1999 | Hojeibane | 6,361,555 B1 | 3/2002 | Wilson |
| 5,938,696 | A | 8/1999 | Goicoechea et al. | 6,383,215 B1 | 5/2002 | Sass |
| 5,948,016 | A | 9/1999 | Jang | 6,387,120 B2 | 5/2002 | Wilson et al. |
| 5,951,599 | A | 9/1999 | McCrory | 6,395,018 B1 | 5/2002 | Castaneda |
| 5,961,548 | A | 10/1999 | Shmulewitz | 6,398,792 B1 | 6/2002 | O'Connor |
| 5,967,986 | A | 10/1999 | Cimochowski et al. | 6,398,804 B1 | 6/2002 | Spielberg |
| 5,972,018 | A | 10/1999 | Israel et al. | 6,428,570 B1 | 8/2002 | Globerman |
| 6,007,517 | A | 12/1999 | Anderson | 6,432,133 B1 | 8/2002 | Lau et al. |
| 6,013,054 | A | 1/2000 | Juin Yan | 6,436,104 B2 | 8/2002 | Hojeibane |
| 6,013,091 | A | 1/2000 | Ley et al. | 6,436,134 B2 | 8/2002 | Richter et al. |
| 6,017,324 | A | 1/2000 | Tu et al. | 6,478,816 B1 | 11/2002 | Kveen et al. |
| 6,017,363 | A | 1/2000 | Hojeibane | 6,482,211 B1 | 11/2002 | Choi |
| 6,030,414 | A | 2/2000 | Taheri | 6,485,511 B2 | 11/2002 | Lau et al. |
| 6,033,434 | A | 3/2000 | Borghi | 6,494,905 B1 | 12/2002 | Zedler et al. |
| 6,033,435 | A | 3/2000 | Penn et al. | 6,511,504 B1 | 1/2003 | Lau et al. |
| 6,036,682 | A | 3/2000 | Lange et al. | 6,511,505 B2 | 1/2003 | Cox et al. |
| 6,039,749 | A | 3/2000 | Marin et al. | 6,520,988 B1 | 2/2003 | Colombo et al. |
| 6,042,597 | A | 3/2000 | Kveen et al. | 6,527,799 B2 | 3/2003 | Shanley |
| 6,045,557 | A | 4/2000 | White et al. | 6,540,719 B2 | 4/2003 | Bigus et al. |
| 6,048,361 | A | 4/2000 | Von Oepen | 6,540,779 B2 | 4/2003 | Richter et al. |
| 6,056,775 | A | 5/2000 | Borghi et al. | 6,572,647 B1 | 6/2003 | Supper |
| 6,059,823 | A | 5/2000 | Holman et al. | 6,579,309 B1 | 6/2003 | Loos et al. |
| 6,059,824 | A | 5/2000 | Taheri | 6,579,312 B2 | 6/2003 | Wilson et al. |
| 6,066,168 | A | 5/2000 | Lau et al. | 6,582,394 B1 | 6/2003 | Reiss et al. |
| 6,068,655 | A | 5/2000 | Sequin et al. | 6,582,459 B1 | 6/2003 | Lau et al. |
| 6,071,285 | A | 6/2000 | Lashinski et al. | 6,596,022 B2 | 7/2003 | Lau et al. |
| 6,086,611 | A | 7/2000 | Duffy et al. | 6,599,316 B2 | 7/2003 | Vardi et al. |
| 6,090,127 | A | 7/2000 | Globerman | 6,689,156 B1 | 2/2004 | Davidson et al. |
| 6,090,128 | A | 7/2000 | Douglas | 6,692,483 B2 | 2/2004 | Vardi et al. |
| 6,096,073 | A | 8/2000 | Webster et al. | 6,706,062 B2 | 3/2004 | Vardi et al. |
| 6,099,497 | A | 8/2000 | Adams et al. | 2001/0012927 A1 | 8/2001 | Mauch |
| 6,117,117 | A | 9/2000 | Mauch | 2001/0016767 A1 | 8/2001 | Wilson et al. |
| 6,117,156 | A | 9/2000 | Richter et al. | 2001/0016768 A1 | 8/2001 | Wilson et al. |
| 6,129,738 | A | 10/2000 | Lashinski et al. | 2001/0027291 A1 | 10/2001 | Shanley |
| 6,129,754 | A | 10/2000 | Kanesaka et al. | 2001/0027338 A1 | 10/2001 | Greenberg |
| 6,142,973 | A | 11/2000 | Carleton et al. | 2001/0029396 A1 | 10/2001 | Wilson et al. |
| 6,152,945 | A | 11/2000 | Bachinski et al. | 2001/0037116 A1 | 11/2001 | Wilson et al. |
| 6,165,195 | A | 12/2000 | Wilson et al. | 2001/0037138 A1 | 11/2001 | Wilson et al. |
| 6,165,197 | A | 12/2000 | Yock | 2001/0037146 A1 | 11/2001 | Lau et al. |
| 6,179,867 | B1 | 1/2001 | Cox | 2001/0037147 A1 | 11/2001 | Lau et al. |
| 6,183,506 | B1 | 2/2001 | Penn et al. | 2001/0039395 A1 | 11/2001 | Mareiro et al. |
| 6,183,509 | B1 | 2/2001 | Dibie | 2001/0039448 A1 | 11/2001 | Dibie |
| 6,190,403 | B1 | 2/2001 | Fischell et al. | 2001/0047201 A1 | 11/2001 | Cox et al. |
| 6,203,569 | B1 | 3/2001 | Wijay | 2001/0049552 A1 | 12/2001 | Richter et al. |
| 6,210,380 | B1 | 4/2001 | Mauch | 2001/0056297 A1 | 12/2001 | Hojeibane |
| 6,210,429 | B1 | 4/2001 | Vardi | 2002/0013618 A1 | 1/2002 | Marotta et al. |
| 6,217,527 | B1 | 4/2001 | Selmon et al. | 2002/0013619 A1 | 1/2002 | Shanley |
| 6,217,608 | B1 | 4/2001 | Penn et al. | 2002/0022874 A1 | 2/2002 | Wilson |
| 6,221,080 | B1 | 4/2001 | Power | 2002/0026232 A1 | 2/2002 | Marotta et al. |
| 6,221,090 | B1 | 4/2001 | Wilson | 2002/0032478 A1 | 3/2002 | Bockstegers et al. |
| 6,221,098 | B1 | 4/2001 | Wilson et al. | 2002/0035392 A1 | 3/2002 | Wilson |
| 6,231,563 | B1 | 5/2001 | White et al. | 2002/0042650 A1 | 4/2002 | Vardi et al. |
| 6,231,598 | B1 | 5/2001 | Berry et al. | 2002/0052648 A1 | 5/2002 | McGuckin et al. |
| 6,231,600 | B1 | 5/2001 | Zhong | 2002/0058990 A1 | 5/2002 | Jang |
| 6,235,051 | B1 | 5/2001 | Murphy | 2002/0072790 A1 | 6/2002 | McGuckin et al. |
| 6,241,762 | B1 | 6/2001 | Shanley | 2002/0107564 A1 | 8/2002 | Cox et al. |
| 6,258,073 | B1 | 7/2001 | Mauch | 2002/0111675 A1 | 8/2002 | Wilson |
| 6,258,099 | B1 | 7/2001 | Mareiro et al. | 2002/0123790 A1 | 9/2002 | White et al. |
| 6,258,116 | B1 | 7/2001 | Hojeibane | 2002/0123797 A1 | 9/2002 | Majercak |
| 6,258,121 | B1 | 7/2001 | Yang et al. | 2002/0123798 A1 | 9/2002 | Burgermeister |
| 6,261,273 | B1 | 7/2001 | Ruiz | 2002/0151959 A1 | 10/2002 | Von Oepen |
| 6,261,305 | B1 | 7/2001 | Marotta et al. | 2002/0156516 A1 | 10/2002 | Vardi et al. |
| 6,261,319 | B1 | 7/2001 | Kveen et al. | 2002/0156517 A1 | 10/2002 | Perouse |
| 6,264,682 | B1 | 7/2001 | Wilson et al. | 2002/0165604 A1 | 11/2002 | Shanley |
| 6,273,911 | B1 | 8/2001 | Cox et al. | 2002/0173835 A1 | 11/2002 | Bourang et al. |

| | | | |
|---|---|---|---|
| 2002/0173840 A1 | 11/2002 | Brucker et al. | |
| 2002/0177892 A1 | 11/2002 | Globerman | |
| 2002/0183763 A1 | 12/2002 | Callol et al. | |
| 2002/0193872 A1 | 12/2002 | Trout et al. | |
| 2002/0193873 A1 | 12/2002 | Brucker et al. | |
| 2003/0004535 A1 | 1/2003 | Musbach et al. | |
| 2003/0009209 A1 | 1/2003 | Hojeibane | |
| 2003/0009214 A1 | 1/2003 | Shanley | |
| 2003/0014102 A1 | 1/2003 | Hong et al. | |
| 2003/0023301 A1 | 1/2003 | Cox et al. | |
| 2003/0050688 A1 | 3/2003 | Fischell et al. | |
| 2003/0074047 A1 | 4/2003 | Richter | |
| 2003/0093109 A1 | 5/2003 | Mauch | |
| 2003/0114912 A1 | 6/2003 | Sequin et al. | |
| 2003/0114915 A1 | 6/2003 | Mareiro et al. | |
| 2003/0125791 A1 | 7/2003 | Sequin et al. | |
| 2003/0125799 A1 | 7/2003 | Limon et al. | |
| 2003/0125802 A1 | 7/2003 | Callol et al. | |
| 2004/0015227 A1 | 1/2004 | Vardi et al. | |

FOREIGN PATENT DOCUMENTS

| | | |
|---|---|---|
| DE | 9014845.2 | 2/1991 |
| DE | 29701758 | 5/1997 |
| EP | 551179 | 7/1993 |
| EP | 684022 | 11/1995 |
| EP | 804907 | 5/1997 |
| EP | 876805 | 11/1998 |
| EP | 884028 | 12/1998 |
| EP | 891751 | 1/1999 |
| EP | 897698 | 2/1999 |
| EP | 897700 | 2/1999 |
| EP | 904745 | 3/1999 |
| EP | 1031328 | 8/2000 |
| EP | 1031330 | 8/2000 |
| EP | 1157674 | 11/2001 |
| EP | 646365 | 1/2004 |
| FR | 2678508 | 1/1993 |
| WO | WO 88/06026 | 8/1988 |
| WO | WO 90/13332 | 11/1990 |
| WO | WO 99/39661 | 8/1991 |
| WO | WO 91/12779 | 9/1991 |
| WO | WO 92/19308 | 11/1992 |
| WO | WO 95/08965 | 4/1995 |
| WO | WO 95/21592 | 8/1995 |
| WO | 96/34580 | 11/1996 |
| WO | WO 96/41592 | 12/1996 |
| WO | WO 97/09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35834 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/15103 | 4/1999 |
| WO | WO 99/17680 | 4/1999 |
| WO | WO 99/34749 | 7/1999 |
| WO | WO 99/36002 | 7/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 2003/055414 | 7/2003 |
| WO | WO 2004/026180 | 4/2004 |

OTHER PUBLICATIONS

Fischmann et al., *The New England Journal of Medicine*, vol. 331, No. 8, pp. 496-501 (1994).

Nakamura et al., *Catheterization & Cardiovascular Diagnosis* 34-353-361 (1995).

Caputo et al., *The American Journal of Cardiology*, vol. 7, pp. 1226-1230 (1996).

Colombo et al., *Catheterization and Cardiovascular Diagnosis*, vol. 30, pp. 327-330 (1993).

Carrie et al., Catheterization and Cardiovascular Diagnosis, vol. 37, pp. 311-313 (1996).

Katoh et al., *Catheterization and Cardiovascular Diagnosis*, vol. 40, pp. 400-402 (1997).

Lewis et al., *American Heart Journal*, vol. 127, pp. 1600-1607 (1994).

Dichek, D.A. et al.; *Circulation*, 80: 1347-1353 (1989).

Chevalier, B. et al.; *American Journal of Cardiology*, 82: 943-949 (1998).

Yamashita, T. et al.; *Journal of American College of Cardiology*, 35: 1145-1151 (2000).

Satler, S., et al.; *Catheterization and Cardiovascular Interventions*, 50: 411-412 (2000).

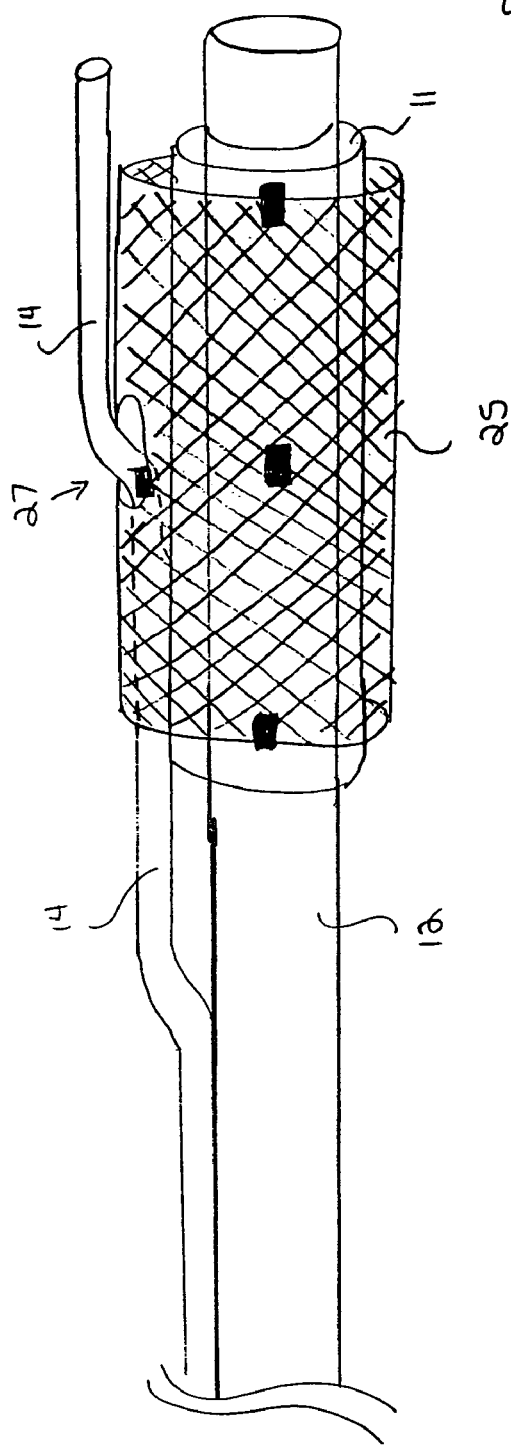

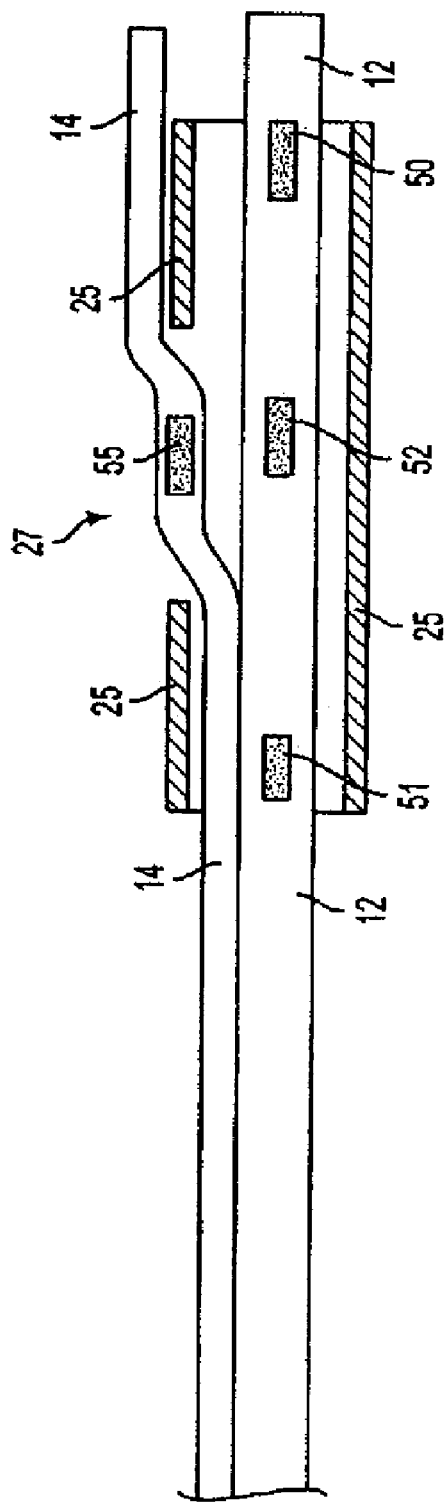

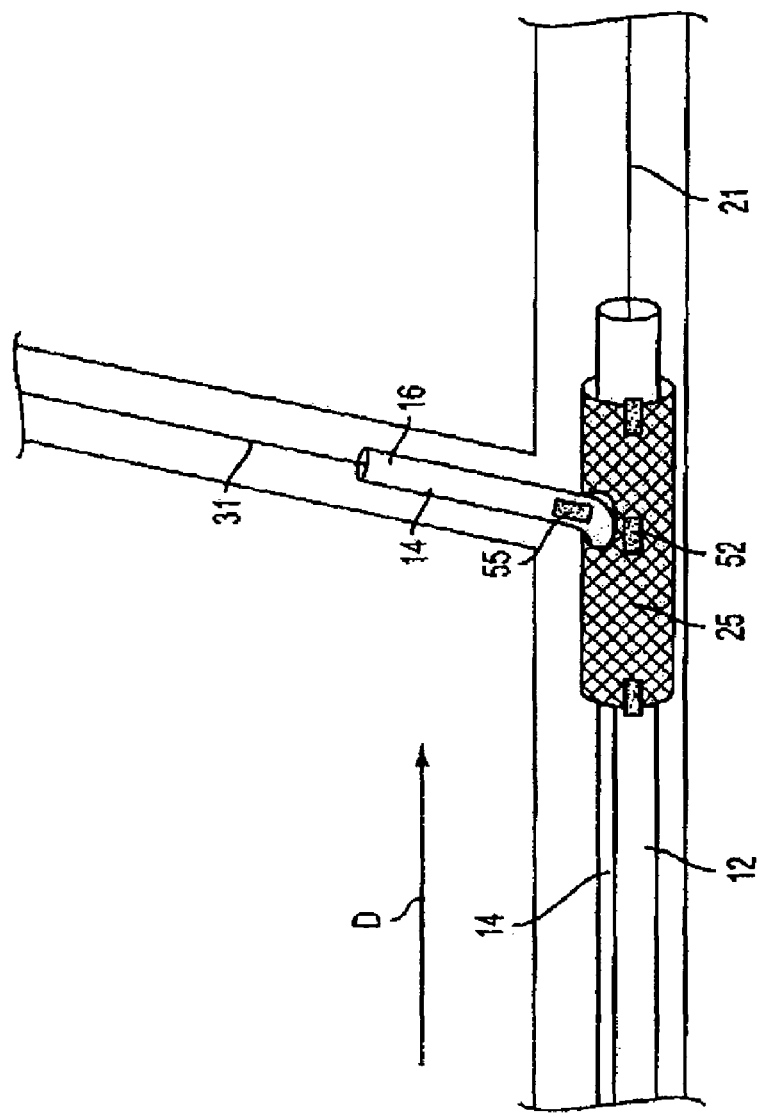

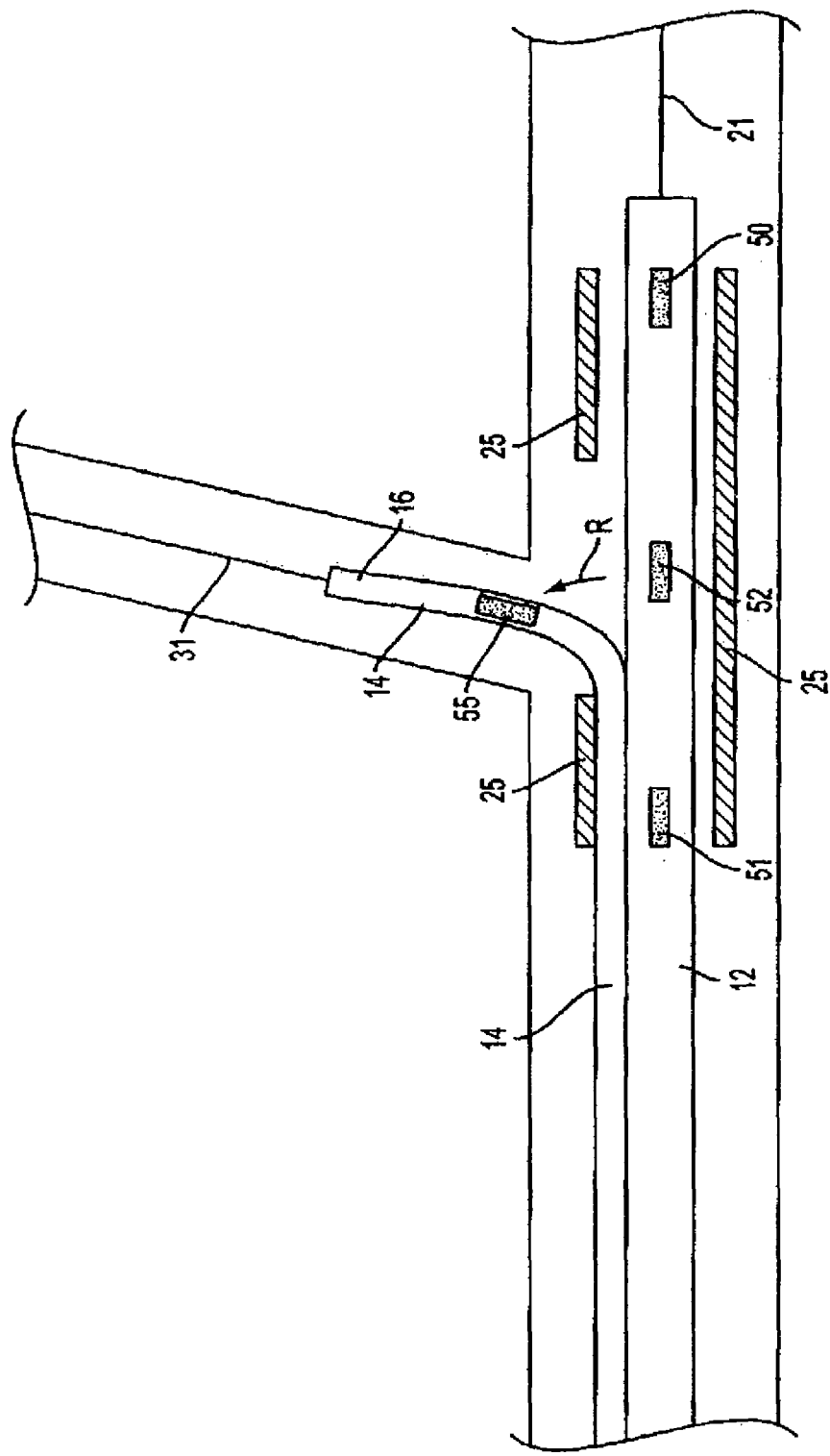

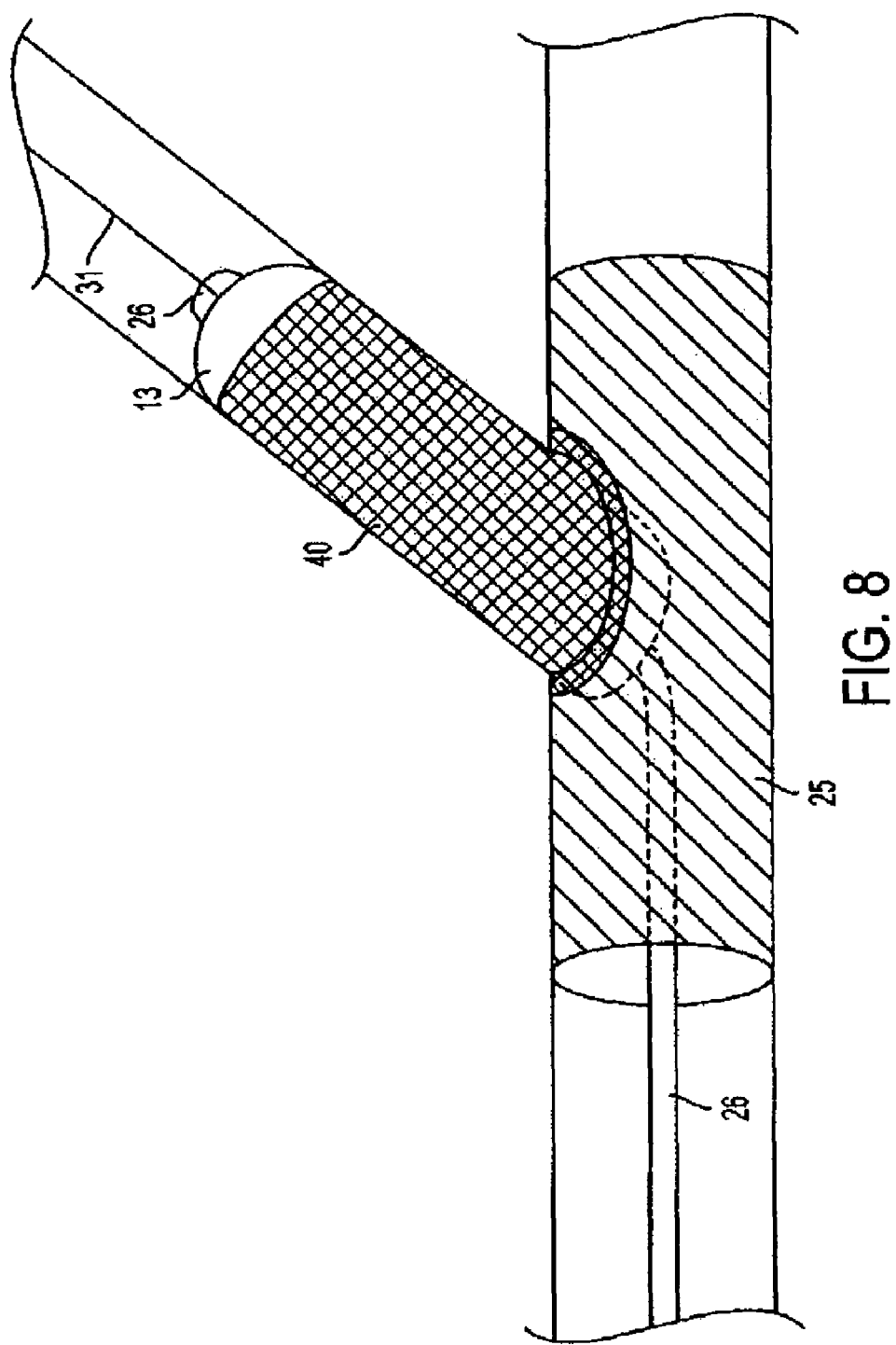

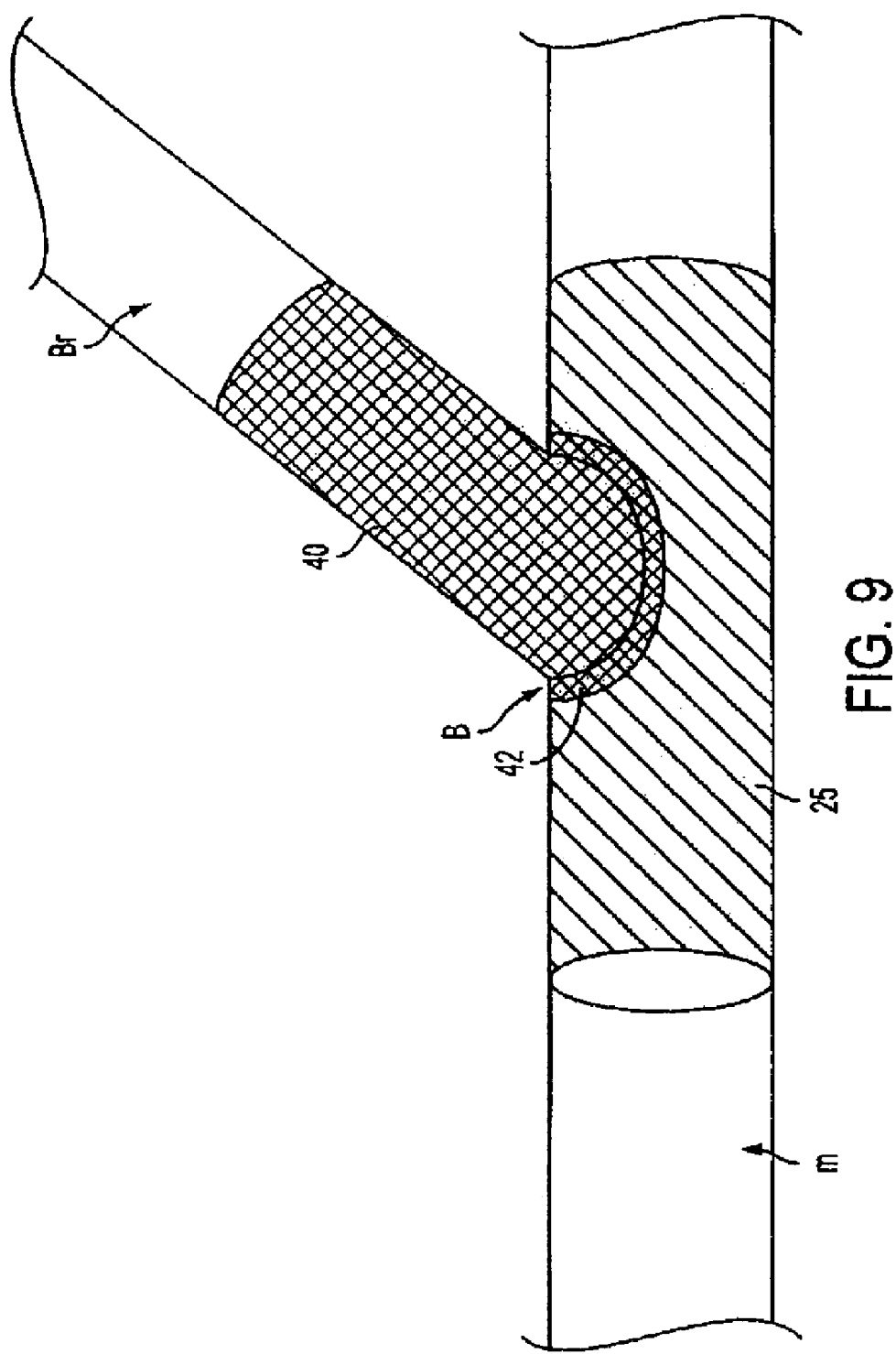

METHOD OF USING A CATHETER WITH ATTACHED FLEXIBLE SIDE SHEATH

CROSS-REFERENCES TO RELATED APPLICATIONS

The present invention is a divisional application of U.S. application Ser. No. 09/455,299, filed on Dec. 6, 1999, now U.S. Pat. No. 6,692,483, issued Feb. 17, 2004, the disclosure of which is hereby incorporated herein by reference.

TECHNICAL FIELD

The present invention relates to catheter systems for delivering stents.

BACKGROUND OF THE INVENTION

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et al., *New England Journal of Medicine* 331: 489-495 (1994) and Fischman, D L et al. *New England Journal of Medicine* 331:496-501 (1994)). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this Application is a device which is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the main vessel and/or its branches, or the bifurcation point and also limits the ability to insert a branch stent into the side branch if the result of treatment of the main, or main, vessel is suboptimal. Suboptimal results may occur as a result of several mechanisms, such as displacing diseased tissue, plaque shifting, vessel spasm, dissection with or without intimal flaps, thrombosis, and embolism.

As described in related copending U.S. patent application Ser. No. 08/744022 filed Nov. 04, 1996, now abandoned; Ser. No. 09/007265 filed Jan. 14, 98; Ser. No. 08/935,383 filed Sep. 23, 1997; and 60/088301 filed Jun. 05, 1998; and PCT patent application Publication No. WO 99/00835 filed Jan. 14, 1998; systems have been developed for deploying a main stent in a main vessel at the intersection of a main vessel and a branch vessel with a branch stent extending into a branch vessel through a side opening in the main vessel. Unfortunately, several difficulties exist when attempting to position such an arrangement of a main and branch stents at a vessel intersection.

For example, the insertion of separate guidewires into both the main vessel and the secondary vessel is required before positioning a main stent in a main vessel with a branch stent projecting through a side opening in the main stent into a branch vessel. Main and branch stents are then advanced over the separate guidewires which have been pre-guided one after another into the respective main and branch vessels, such that the main stent can be deployed within the main vessel and the branch stent can be deployed through the side opening in the main stent into the branch vessel. Unfortunately, when attempting to guide two such separate guidewires through the main vessel such that one enters the branch vessel, the two guidewires typically tend to wrap around one another and become entangled. Additionally, time and effort is required to individually position each of the two guidewires one after another.

An additional disadvantage of conventional stents is the difficulty in visualizing the stents during and after deployment, and in general, the fact that they are not readily imaged by low-cost and easy methods, such as x-ray or ultrasound imaging.

SUMMARY OF THE INVENTION

The present invention provides a stent delivery system which comprises a catheter with a flexible side sheath attached thereto. In a preferred aspect of the invention, the catheter is adapted to receive a first guidewire therethrough, and the flexible side sheath is adapted to receive a second guidewire therethrough.

As will be explained, an advantage of the present stent delivery system is that it may be used for deploying a main stent in a main vessel with a side opening in the main stent being aligned with the ostium of a branch vessel. In additional preferred aspects, a branch stent can also be deployed in the branch vessel with the branch stent passing through the side opening in the main stent.

Accordingly, the present invention also sets forth methods of positioning a main stent at a vessel bifurcation such that a side opening in the main stent is positioned at the ostium of a branch vessel. In preferred aspects, a main guidewire is first positioned in the main vessel such that a distal end of the main guidewire extends past the bifurcation. Thereafter, the stent delivery system, (comprising a catheter with an attached flexible side sheath), is advanced to a position proximate the bifurcation, wherein the catheter is advanced over the main guidewire, and wherein the main stent is positioned over the catheter. In preferred aspects, the flexible side sheath is positioned to pass through the interior of the main stent, (positioned over the distal end of the catheter), and out of the side opening in the main stent.

Thereafter, a branch guidewire is advanced through the flexible side sheath and into the branch vessel. To assist in guiding the second guidewire into the branch vessel, the flexible side sheath may preferably taper to a narrow distal end, which may be curved slightly outwardly.

Subsequently, the stent delivery system is advanced with the catheter advancing over the main guidewire while the flexible side sheath concurrently advances over the branch guidewire. In one aspect of the invention, the side opening in the main stent is positioned in alignment with the ostium of the branch vessel due solely to the presence of the branch guidewire extending from an interior of the main stent out through the side opening in the main stent and into the branch vessel.

In another more preferred aspect of the invention, however, the side opening in the main stent is positioned in alignment with the ostium of the branch vessel by viewing relative movement of radiopaque markers positioned on each of the catheter and the flexible side sheath. In this aspect of the invention, the relative marker movement indicates that a portion of the flexible side sheath which is positioned adjacent the side opening in the main stent is advancing into the ostium of the branch vessel, thereby indicating the position of the side opening of the main stent with respect to the ostium of the branch vessel. In this aspect of the invention, the flexible side sheath will deflect into the branch vessel as it is advanced over the second guidewire, (while the catheter itself moves distally along through the main vessel over the first guidewire).

Such relative movement of the radiopaque markers may be viewed as a rotation of a marker on the flexible side sheath with respect to a marker(s) on the catheter, or as a separation between the marker on the flexible side sheath with respect to a marker(s) on the catheter. In certain aspects, the marker on the flexible side sheath is positioned adjacent a marker on the catheter, such that the relative marker motion will be viewable in an image as a separation occurring between the two markers. In a preferred aspect of the invention, the relative movement of the markers on the catheter and flexible side sheath can be observed fluoroscopically as the markers are radiopaque and are preferably made of suitable materials including tungsten and gold.

In addition, a plurality of markers may be positioned on the catheter with a marker positioned at locations corresponding to each of the proximal and distal ends of the main stent. A medial marker may also be included, positioned halfway between the distal and proximal markers, for indicating the position of the side hole in the main stent, (which is preferably positioned halfway between the distal and proximal ends of the stent).

In additional aspects of the present invention, the main stent is deployed in the main vessel, (such as by an inflatable balloon at the distal end of the catheter). Thereafter, a branch stent may be advanced through the at least partially deployed main stent and positioned in the branch vessel. Preferably, the branch stent is advanced through the at least partially deployed main stent by a second catheter, which then deploys the branch stent in the branch vessel, (such as by an inflatable balloon at the distal end of the second catheter).

To deploy the branch stent, the delivery system, (comprising the catheter and attached flexible side sheath), may be removed leaving the two guidewires in place such that the second catheter can then be advanced over the second guidewire and into the branch vessel. As such, the second catheter can then be advanced over the second guide wire with its distal end extending into the branch vessel.

An advantage of the present stent delivery system is that it avoids having to separately position first and second guidewires within the respective main and branch vessels prior to deployment of the main and branch stents thereover. Rather, with the present invention, only a single guidewire needs to initially be placed within the main vessel, with the delivery system subsequently deploying both the main and branch stents thereover.

The main stent may optionally include outwardly expandable portions which can be expanded from an initial position which is flush with the cylindrical body of the stent to protrude outwardly from the side opening in the main stent, thereby anchoring into the walls of the branch vessel, holding the side opening in registry with the ostium of the branch vessel. In an exemplary aspect, the cylindrical body of the main stent has an even surface, with an expandable portion positioned within the side opening of the cylindrical body, such that it is flush with the cylindrical body prior to expansion.

In addition, the branch stent may optionally comprise a contacting portion at its proximal end to secure the proximal end of the branch stent to the side opening in the main stent. In an exemplary aspect, the contacting portion comprises a flared proximal end.

Applications of the present system include the cardiac, coronary, renal, peripheral vascular, gastrointestinal, pulmonary, urinary and neurovascular systems and the brain. Further advantages of the present stent delivery system are that it provides an improved stent delivery apparatus, which may deliver main and branch stents to: 1) completely cover the bifurcation point of bifurcation vessels; 2) be used to treat lesions in one branch of a bifurcation while preserving access to the other branch for future treatment; 3) allow for differential sizing of the stents in a bifurcated stent apparatus even after a main stent is implanted; 4) treat bifurcation lesions in a bifurcated vessel where the branch vessel extends from the side of the main vessel; and 5) be marked with, or at least partly constructed of, material which is imageable by commonly used intraluminal catheterization visualization techniques including but not limited to ultrasound or x-ray.

BRIEF DESCRIPTION OF THE DRAWINGS

FIG. 2A is a close up illustration of the distal end of the stent delivery system of FIG. 1 with a main stent positioned thereon.

FIG. 2B is a sectional side elevation view corresponding FIG. 2A.

FIG. 6A is an illustration of the catheter and attached flexible side sheath advanced over the first and second guidewire such that the distal end of the flexible side sheath is deflected into the branch vessel, showing the separation between radiopaque markers on the catheter and flexible side sheath.

FIG. 6B is a sectional side elevation view corresponding FIG. 6A.

FIG. 8 is an illustration of the deployment of the branch stent by a balloon disposed on a second catheter received over the second guidewire.

FIG. 9 is an illustration of the fully deployed main and branch stents with the guidewires and stent delivery system removed.

DESCRIPTION OF THE SPECIFIC EMBODIMENTS

The present invention comprises methods of positioning a main stent at a vessel bifurcation such that a side opening in the main stent is positioned at the ostium of a branch vessel, and sets forth various apparati and kits for performing the preferred methods.

In addition, the present invention comprises methods for positioning a main and a branch stent at a vessel bifurcation, wherein the branch stent is deployed through a side opening in the main stent, with the side opening in the main stent being positioned in registry with the ostium of the branch vessel.

Figure 1:
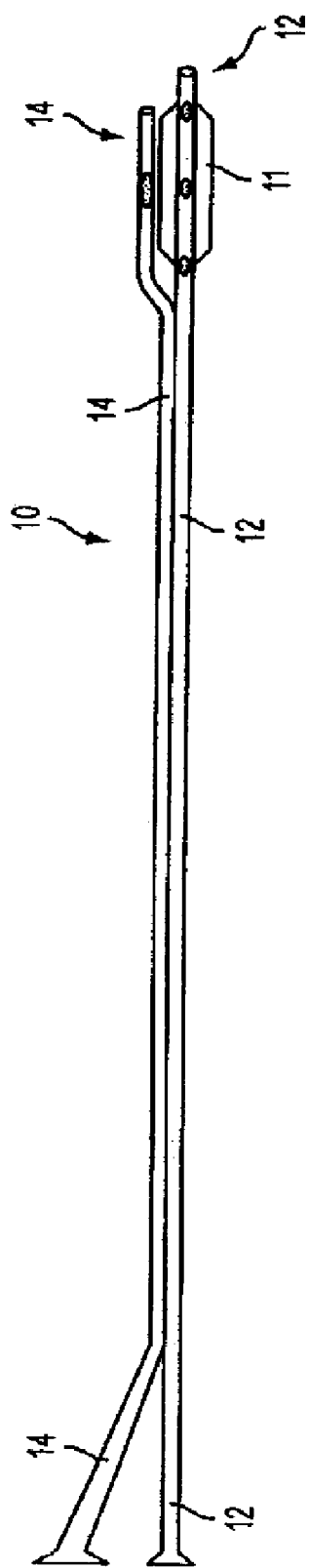
FIG. 1 is an illustration of the present stent delivery system, showing a catheter with a flexible side sheath attached thereto.
Figure 5:
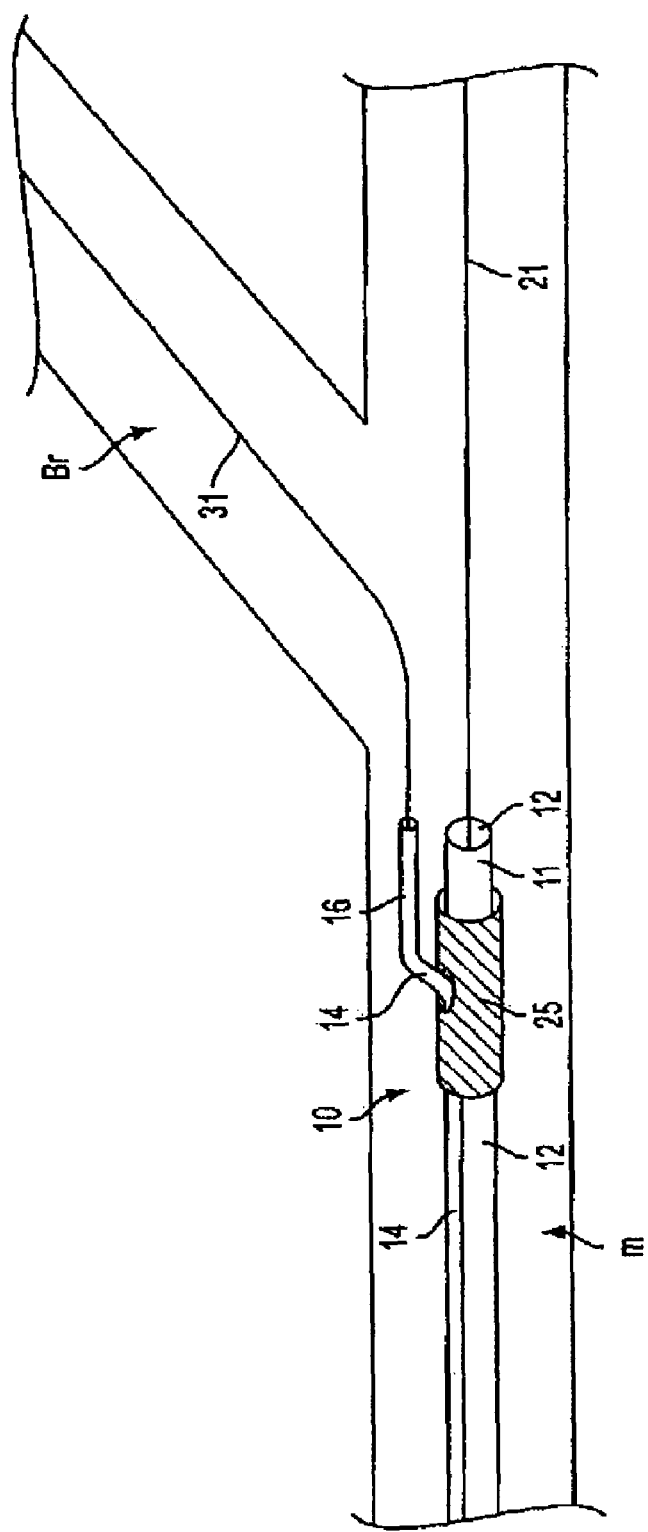
FIG. 5 is an illustration of the second guidewire being advanced out of the distal end of the side sheath, through a side opening in a main stent and into the branch vessel.

A novel stent delivery system is provided for accomplishing the preferred methods. Referring to FIGS. 1 to 2B, the present stent delivery system 10 comprises a first catheter 12 having an attached flexible side sheath 14. An inflatable balloon 11 is preferably positioned at the distal end of first catheter 12. As is shown in FIGS. 5 to 6B, first catheter 12 is receivable over a first guidewire 21 and flexible side sheath 14 is receivable over a second guidewire 31. As can be seen, stent 25 is preferably crimped down onto flexible side sheath 14, as shown. Preferably, stent 25 is initially crimped onto balloon 11 with distal end 16 of side sheath 16 projecting outwardly through side opening 27 as shown.

The present invention provides a method of positioning a main stent 25 at a vessel bifurcation B such that a side opening 27 in main stent 25 is positioned at the ostium of a branch vessel Br, as follows.

Figure 3:
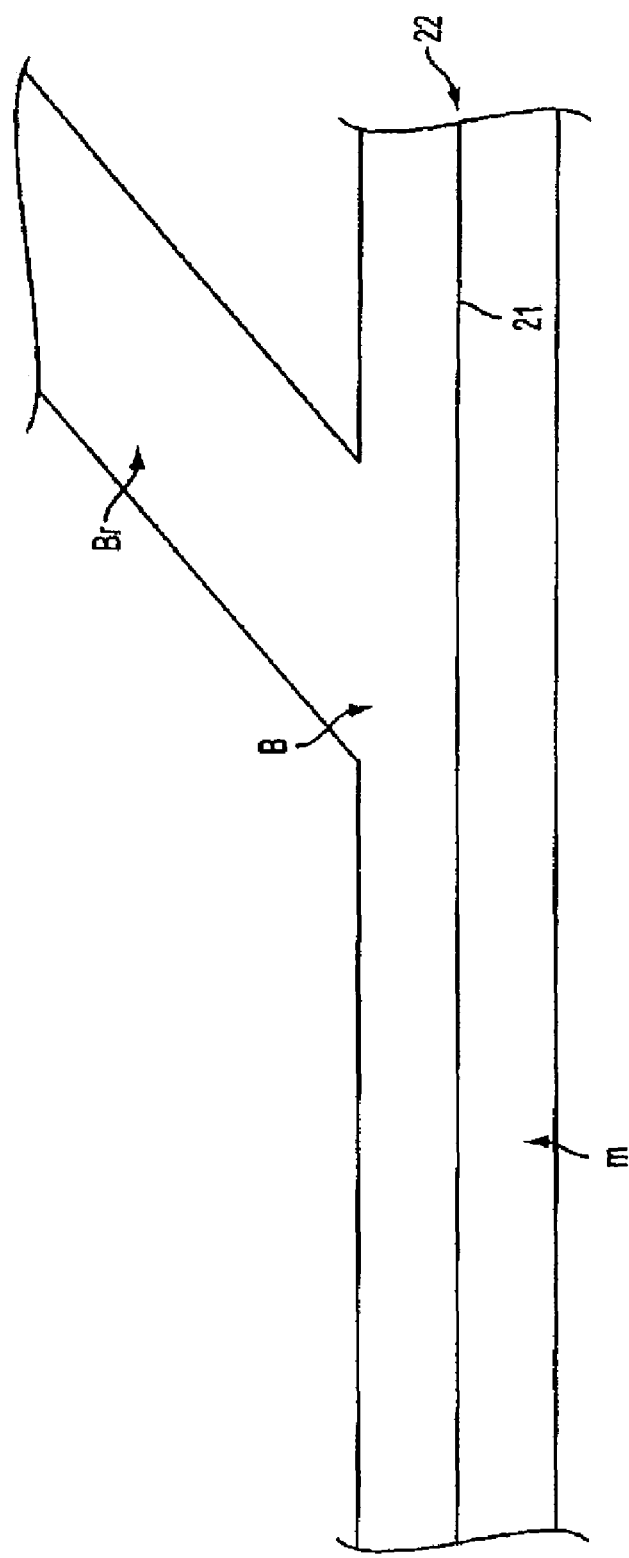
FIG. 3 is an illustration of a placement of first guidewire within a main vessel.
Figure 4:
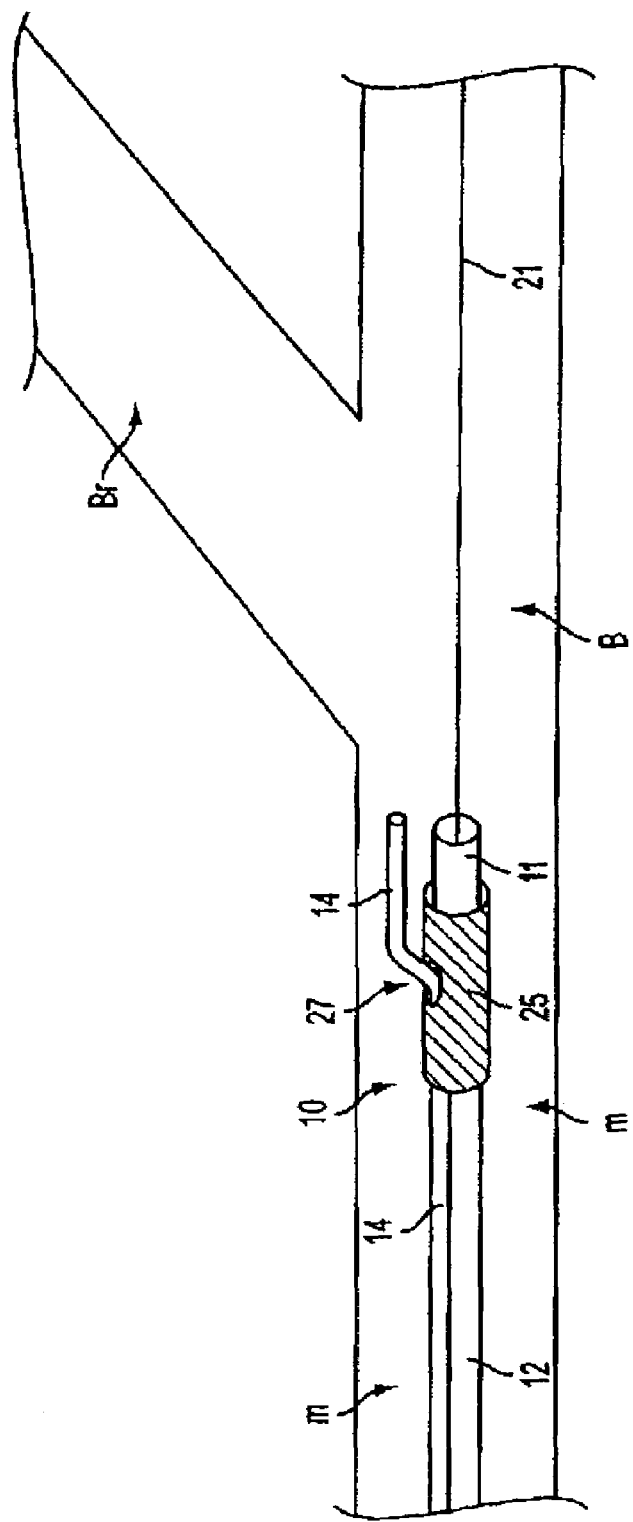
FIG. 4 is an illustration of the catheter and attached flexible side sheath of the present invention advanced over the first guidewire to a position near the ostium of the branch vessel.

Referring to FIG. 3, a main guidewire 21 is first positioned in the main vessel M such that a distal end 22 of main guidewire 21 extends past bifurcation B. Referring to FIG. 4, stent delivery system 10 is then advanced to a position proximate bifurcation B, wherein catheter 12 is received over first guidewire 21, and wherein main stent 25 is positioned over catheter 12 with flexible side sheath 14 positioned to pass through the interior of main stent 25 and out of side opening 27 in main stent 25, as shown. Referring to FIG. 5, second guidewire 31 is then advanced through flexible side sheath 14 attached to catheter 12 and into branch vessel Br.

In one aspect of the invention, side opening 27 in main stent 25 is positioned in alignment with the ostium of branch vessel Br simply by the presence of second guidewire 31 extending from an interior of main stent 25 out through side opening 27 in main stent 25 and into branch vessel Br. In this aspect of the invention, the insertion of a branch stent over guidewire 31 through side opening 27 in main stent 25 and into branch vessel Br serves to align the side opening 27 with the ostium of branch vessel Br.

In another more preferred aspect, however, stent delivery system 10, (comprising catheter 12 and attached flexible side sheath 14), are subsequently advanced distally in direction D to the position as shown in FIGS. 6A and 6B, with catheter 12 being advanced over first guidewire 21 while flexible side sheath 14 is advanced over second guidewire 31. In this aspect of the invention, an operator views relative movement between a radiopaque marker positioned on the flexible side sheath with respect to at least one radiopaque marker positioned on the catheter, wherein the relative marker movement indicates that a portion of the flexible side sheath adjacent the side opening in the main stent is advancing into the ostium of the branch vessel, thereby indicating the position of the side opening of the main stent with respect to the ostium of the branch vessel.

Specifically, referring to FIGS. 2B and 6B, a distal marker 50, a proximal marker 51 and a medial marker 52 may be disposed on catheter 12. Preferably, the location of proximal marker 51 corresponds to the location of the proximal end of stent 25, the location of distal marker 50 corresponds to the location of the distal end of stent 25, and the location of medial marker 52 corresponds to the location of side opening 27 of stent 25. At least one marker 55 is positioned on flexible side sheath 14 as shown. Preferably, marker 55 is positioned adjacent to medial marker 52.

As can be seen by comparing FIGS. 2B to 6B, as stent delivery system 10 is advanced distally such that the distal end of flexible side sheath 14 is received in branch vessel Br, (FIG. 6B), marker 55 will move in direction R relative to markers 50, 51 and 52. In particular, an increasing separation distance will occur between marker 55 positioned on flexible side sheath 14 and marker 52 positioned on catheter 12 as catheter 12 is advanced distally over first guidewire 21 while flexible side sheath 14 is simultaneously advanced distally over second guidewire 31.

In an additional aspect of the invention, each of marker 52 and 55 are slightly elongated and rectangle shaped, (as shown), such that relative rotational movement therebetween can also be observed. Marker 55 may be made of tungsten and markers 50, 51 and 52 may be made of gold.

When the operator views the relative motion between markers 52 and 55, this indicates that the portion of flexible side sheath 14 positioned adjacent side opening 27 is disposed at the ostium of branch vessel Br. By viewing the position of markers 50, 51 and 52, the operator can also determine the position of the distal and proximal ends of stent 25 and the position of side opening 27 with respect to the ostium of branch vessel Br.

The present invention also comprises systems for deploying a branch stent into branch vessel Br with main stent 25 positioned such that side opening 27 is in registry with the ostium of branch vessel Br. In these aspects of the invention, as illustrated in FIGS. 7 through 10, branch stent 40 is advanced through the interior of main stent 25, passing through side opening 27 and into branch vessel Br.

Figure 7A:
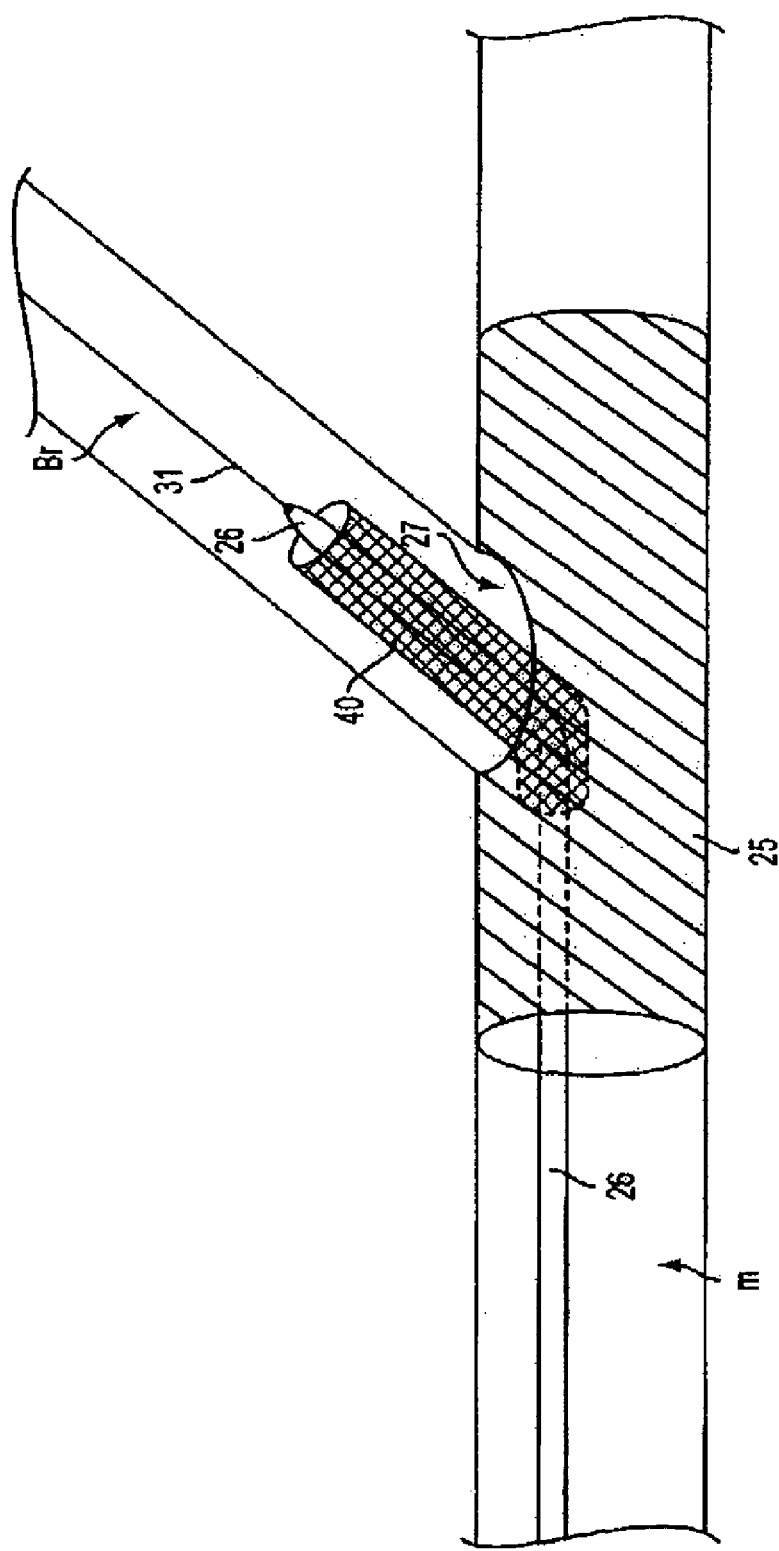
FIGS. 7A and 7B is an illustration of a branch stent advanced over the second guidewire and through the side opening in the main stent and into the branch vessel.

FIG. 7A is an illustration of branch stent 40, (disposed on the distal end of a second catheter 26), being advanced over second guidewire 31, passing through side opening 27 in main stent 25 into branch vessel Br. As can be seen, in one aspect of the present invention, stent delivery system 10 may first fully deploy main stent 25 and then be removed. Thereafter, second catheter 26 can be advanced over second guidewire 31 to position stent 40 for deployment in the branch vessel.

Figure 7B:
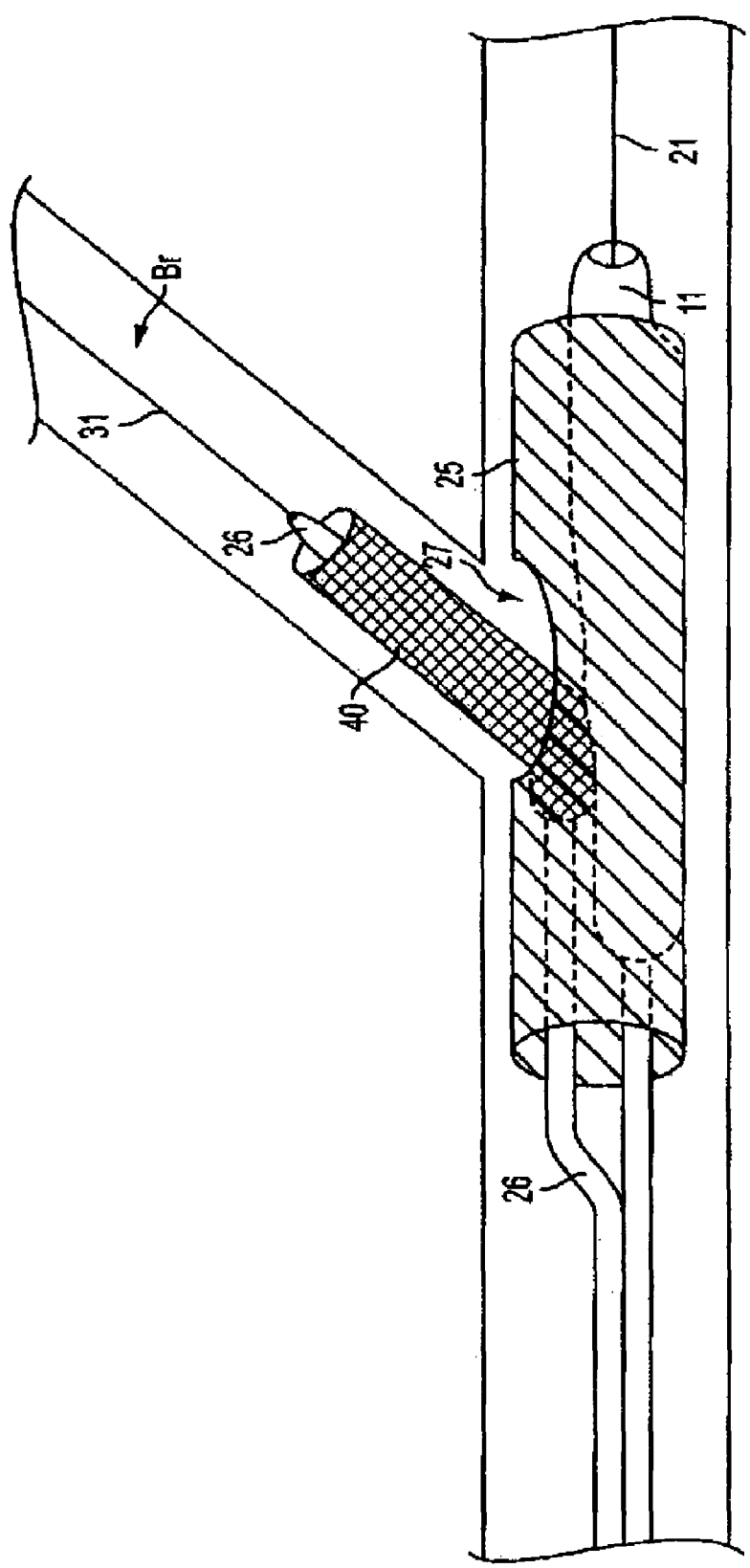

In an alternative aspect of the invention, as shown in FIG. 7B, stent 25 may be partially deployed in main vessel M and second catheter 26 may then be advanced through the partially expanded interior of main stent 25, passing out through side opening 27 in main stent 25 while stent delivery system 10 remains adjacent bifurcation B.

FIG. 8 is an illustration of the deployment of branch stent 40 by a balloon 13 disposed on the distal end of second catheter 26, which is itself received over second guidewire 31. In this aspect of the invention an inflatable balloon 13 disposed at the distal end of second catheter 26 is used to deploy branch stent 40.

FIG. 9 is an illustration of the fully deployed main and branch stents 25 and 40 with the guidewires (21 and 31) and stent delivery system (10) removed. As can also be seen, stent 40 may further comprise a contact portion 42 which remains disposed within side opening 27 thereby securing the proximal end of stent 40 to side opening 27 of stent 25, thereby providing a bifurcated stent arrangement covering vessel bifurcation B. Such a contacting portion 42 is further described in copending PCT Patent Application WO 99/00835, filed Jan. 14, 1998.

Figure 10:
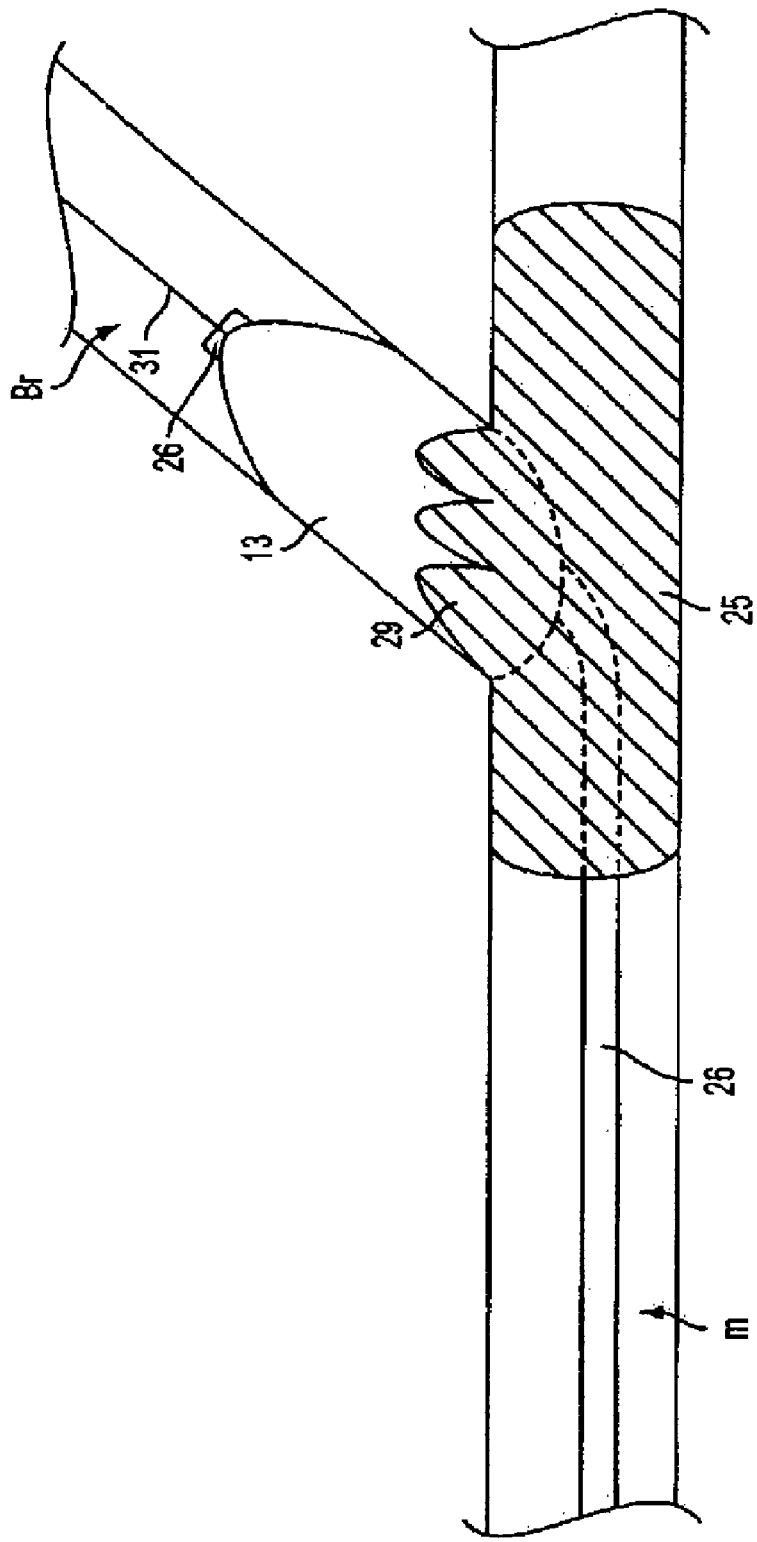
FIG. 10 shows an embodiment of the present invention with outwardly expandable portions disposed around the side opening on the main stent.

Lastly, FIG. 10 shows an embodiment of the present invention with outwardly expandable portions disposed around the side opening on the main stent. Specifically, balloon 13 on catheter 26 can also be inflated to deploy radially expandable portions 29 which extend laterally outward from an initial position flush with the cylindrical body of stent 25 to a position where portions 29, (disposed around the edges of side opening 27), are anchored against the walls of branch vessel B, such that side opening 27 is positioned in registry with the ostium of branch vessel B. Further description of such radially expandable portions 29 which extend laterally outward from the edges of side opening 27 is set forth in Published PCT patent application No. WO 99/00835 filed Jan. 14, 1998, incorporated herein by reference in its entirety.

The present invention also comprises kits including the apparatus of the present invention with instructions for use setting forth any of the herein disclosed methods for use.

What is claimed is:

1. A method of positioning a main stent in a main vessel at a vessel bifurcation such that a side opening in the main stent is positioned at an ostium of a branch vessel, the method comprising:

positioning a main guidewire in the main vessel such that a distal end of the main guidewire extends past the vessel bifurcation:

advancing a stent delivery system over the main guidewire to a position proximate the bifurcation, the stent delivery system comprising a catheter with a flexible side sheath attached thereto, wherein the catheter is received over the main guidewire, and wherein the main stent is positioned over the catheter with the flexible side sheath positioned to pass through an interior of the main stent and out the side opening in the main stent, the flexible side sheath having a distal end portion extending distal of the side opening of the stent;

subsequently, advancing a branch guidewire through the flexible side sheath attached to the catheter and into the branch vessel;

subsequently, advancing the catheter over the main guidewire while advancing the flexible side sheath over the branch guidewire, wherein the distal end portion of the flexible side sheath advances into the branch vessel; and viewing relative movement of a marker positioned on the distal end portion of the flexible side sheath with respect to at least one marker positioned on the catheter when advancing the flexible side sheath over the branch guidewire, wherein the relative movement indicates that the distal end portion of the flexible side sheath is advancing into the ostium of the branch vessel, thereby indicating a relative position of the side opening of the main stent with respect to the ostium of the branch vessel, wherein viewing the at least one marker positioned on the catheter comprises viewing markers positioned adjacent the distal and proximal ends of the main stent.

* * * * *